United States Patent
Fauda et al.

(10) Patent No.: US 11,208,925 B2
(45) Date of Patent: Dec. 28, 2021

(54) DIAGNOSTIC SYSTEM FOR A LUBRICATION CIRCUIT

(71) Applicant: VHIT S.p.A. Societa Unipersonale, Offanengo (IT)

(72) Inventors: Alessandro Fauda, Treviglio (IT); Gabriele Andreolli, Isera (IT); Leonardo Cadeddu, Crema (IT); Luciano Marchetti, Montodine (IT); Pietro Francesco Crosio, Stradella (IT)

(73) Assignee: VHIT S.P.A. SOCIETÀ UNIPERSONALE, Offanengo (IT)

( * ) Notice: Subject to any disclaimer, the term of this patent is extended or adjusted under 35 U.S.C. 154(b) by 0 days.

(21) Appl. No.: 16/652,339

(22) PCT Filed: Oct. 15, 2018

(86) PCT No.: PCT/EP2018/077999
§ 371 (c)(1),
(2) Date: Mar. 30, 2020

(87) PCT Pub. No.: WO2019/081242
PCT Pub. Date: May 2, 2019

(65) Prior Publication Data
US 2020/0232356 A1 Jul. 23, 2020

(30) Foreign Application Priority Data
Oct. 25, 2017 (IT) .......... 102017000121455

(51) Int. Cl.
*G01N 33/28* (2006.01)
*F01M 1/18* (2006.01)
(Continued)

(52) U.S. Cl.
CPC ......... *F01M 11/10* (2013.01); *G01N 33/2888* (2013.01); *F01M 1/18* (2013.01);
(Continued)

(58) Field of Classification Search
CPC ............................................. F01M 2011/1486
See application file for complete search history.

(56) References Cited

U.S. PATENT DOCUMENTS 5,076,397 A * 12/1991 Yamada ................. F16N 29/00
184/108
6,213,080 B1 * 4/2001 Marsh ................ F01M 11/0458
123/196 R
(Continued)

FOREIGN PATENT DOCUMENTS

FR  2872543 A1  1/2006
FR  3017652 A1  8/2015

OTHER PUBLICATIONS

International Search Report for PCT/EP2018/077999, dated Jan. 4, 2019.

*Primary Examiner* — Herbert K Roberts
(74) *Attorney, Agent, or Firm* — Norton Rose Fulbright US LLP; Gerard Messina

(57) ABSTRACT

A diagnostic system for a lubrication circuit of an internal combustion engine of a vehicle. The system includes a viscometer for detecting the viscosity of a lubricating liquid of the lubrication circuit, a temperature sensor for detecting the temperature of the lubricating liquid, and a control unit to acquire the state of the lubricating liquid, given by the viscosity detected for a given lubricating liquid condition, which includes the lubricating liquid temperature and the date of last replacement of the lubricating liquid, and for a given condition of use of the engine, and to assess the state of the lubricating liquid by comparing the detected viscosity of the lubricating liquid with the viscosity reference values stored in the database in the same or similar condition of lubricating liquid temperature, date of last replacement of the lubricating liquid and use of the engine.

9 Claims, 1 Drawing Sheet

(51) Int. Cl.
*F01M 11/10* (2006.01)
*F16N 29/04* (2006.01)

(52) U.S. Cl.
CPC ........ *F01M 2011/148* (2013.01); *F16N 29/04* (2013.01); *F16N 2250/08* (2013.01); *F16N 2250/36* (2013.01)

(56) References Cited

U.S. PATENT DOCUMENTS

| | | |
|---|---|---|
| 2003/0172722 A1 | 9/2003 | Jakoby |
| 2006/0114007 A1* | 6/2006 | Cho .................. G01N 33/2888 324/698 |
| 2008/0223114 A1 | 9/2008 | Albertson et al. |
| 2009/0283364 A1 | 11/2009 | Throop et al. |
| 2011/0041796 A1* | 2/2011 | Sachdev ............... F01M 11/03 123/196 A |
| 2012/0006289 A1 | 1/2012 | Petz et al. |
| 2012/0316752 A1 | 12/2012 | Krishevsky |
| 2013/0167507 A1* | 7/2013 | Barucchi ................ F01N 9/002 60/274 |
| 2013/0342150 A1* | 12/2013 | Ozaki ................ B60L 15/2072 318/490 |
| 2016/0201533 A1* | 7/2016 | Upadhyay .............. F01N 9/002 701/102 |

* cited by examiner

DIAGNOSTIC SYSTEM FOR A LUBRICATION CIRCUIT

FIELD

The present invention generally relates to a diagnostic system for a lubrication circuit of internal combustion engines. More particularly, the diagnostic system is based on the detection of the viscosity of lubricating liquid of the lubrication circuit. The diagnostic system finds application especially in the automotive field.

BACKGROUND INFORMATION

In the automotive field, a lubricating liquid is conventionally used for lubricating internal combustion engines by means of suitable lubrication circuits. In addition to lubricating the moving parts of an engine, the lubricating liquid also performs the function of keeping the engine clean, protecting it from corrosion, improving sealing thereof and cooling it by discharging the heat from the moving parts.

The lubricating liquid undergoes a deterioration process during its use and therefore it must be replaced periodically. The most common current systems provide for the replacement of the lubricating liquid on the basis only of the kilometers traveled by the vehicle. However, the kilometers traveled by the vehicle do not provide a reliable measure of the actual state of the lubricating liquid, and therefore do not allow a correct evaluation of the capacity of the same to adequately fulfill its functions.

In order to solve this problem, solutions are provided according to which the evaluation of the lubricant is based on the measurement of its viscosity and temperature. For instance, United States Patent Application Pub. No. US 2012/0316752 A1 describes a device for a motor vehicle comprising a viscometer, connected to the lubrication circuit and adapted to measure the viscosity of the lubricating liquid, and a temperature sensor, suitable for measuring the temperature of the lubricating liquid. The viscosity, measured both with the engine off and with the engine running, is compared with expected values and the results are shown in the instrument panel.

The conventional device, however, basing the evaluation of the lubricating liquid on the viscosity and temperature thereof, does not allow an accurate assessment of the state of the lubricating liquid.

An object of the present invention is to overcome the problems and limitations of conventional devices by providing a diagnostic system capable of assessing the state of the lubricating liquid more accurately.

This and other objects may be achieved with an example vacuum assembly in accordance with the present invention.

SUMMARY

An example diagnostic system for a lubrication circuit of an internal combustion engine of a vehicle according to the present invention includes a viscometer adapted to detect the viscosity of a lubricating liquid of the lubrication circuit, and a temperature sensor adapted to detect the temperature of the lubricating liquid.

The example diagnostic system further an arrangement for acquiring the date of last replacement of the lubricating liquid and an arrangement for determining the instantaneous condition of use of the engine at the time of detection.

A non-exhaustive and non-exclusive set of arrangements for determining the condition of use of the engine includes, for example, sensors adapted to detect the rotation speed of the motor shaft, the torque and/or the power of the engine, the speed of the vehicle, the distance traveled by the vehicle and the temperature outside the engine.

The sensors are usually already present on the vehicle engine: all of their measurements in predefined conditions (for example, at different engine rotation speeds or at different levels of delivered power), defined during the engine calibration phase, allow to create a series of reference mappings for the condition of use of the engine.

The example diagnostic system further includes a database capable of storing viscosity reference values for at least a given temperature of the lubricating liquid, a given date of last replacement of the lubricating liquid, and a given condition of use of the engine.

The example diagnostic system is further equipped with a control unit capable of acquiring the state of the lubricating liquid. The state of the liquid is given by the viscosity of the lubricating liquid detected for a given condition of the lubricating liquid, comprising the temperature of the lubricating liquid and the date of last replacement of the lubricating liquid, and for a given condition of use of the engine, as described above. The control unit is also adapted to evaluate the state of the lubricating liquid by comparing the detected viscosity of the lubricating liquid with the reference viscosity values stored in the database, in the same or similar temperature condition of the lubricating liquid, date of last liquid replacement of the lubricating liquid and use of the engine.

In accordance with a further feature of the present invention, the control unit is configured to activate, depending on the detected state of the lubricating liquid, a signal indicating that replacement of the lubricating liquid is required.

In accordance with a further feature of the present invention, the control unit is configured to control, depending on the detected state of the lubricating liquid, actuation of a regeneration cycle of a filter of the lubrication circuit, and, based on information about the path that the vehicle will have to travel, to determine a section of said path in which it is preferable to actuate said regeneration cycle of the filter.

In accordance with a further feature of the present invention, the control unit is configured to activate, depending on the state of the lubricating liquid, a signal aboard the vehicle indicating that reduction of the vehicle speed is required.

In accordance with a further feature of the present invention, the control unit is configured to activate, depending on the state of the lubricating liquid, a "recovery" mode of the internal combustion engine in which the engine operates at low speeds.

In accordance with a further feature of the present invention, the control unit is configured to vary, depending on the state of lubricant liquid state and on the use of the vehicle, the flow rate of the lubricating liquid supplied to the engine.

In accordance with a further feature of the present invention, the control unit is configured to generate, depending on the state of the lubricating liquid, a signal indicating that addition of additives to the lubricating liquid is required.

In accordance with a further feature of the present invention, the control unit is configured to activate an addition of additives to the lubricating liquid, said additives being dispensable by a suitable additive tank connected to the lubrication circuit.

BRIEF DESCRIPTION OF EXAMPLE EMBODIMENTS

These and other features and advantages of the present invention will become more apparent from the following description of preferred embodiments of the present invention, given by way of non-limiting example with reference to the figures, in which elements indicated by the same or similar reference numeral indicate elements having the same of similar functionality and structure.

DESCRIPTION OF SOME PREFERRED
EMBODIMENTS OF THE INVENTION

Figure 1:
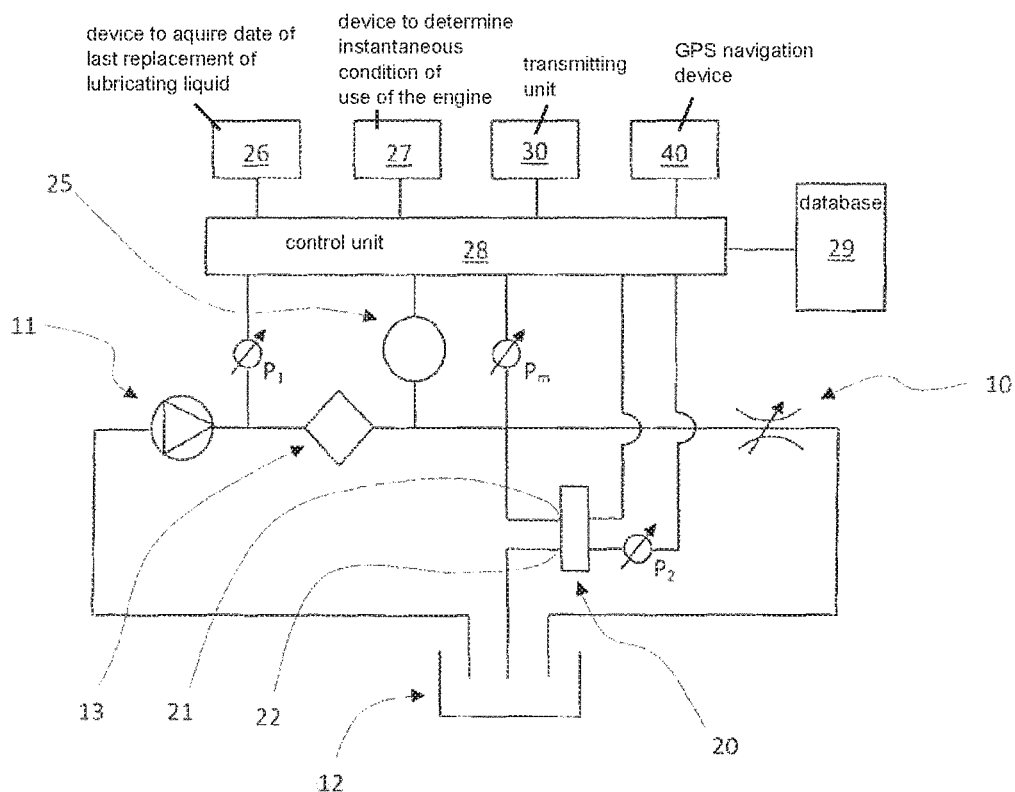
FIG. 1 is a schematic view showing an example diagnostic system of a lubrication circuit according to the present invention.

Referring to FIG. 1, a diagnostic system is applied to a lubrication circuit of a combustion engine (engine) 10 of a vehicle.

The lubrication circuit includes, in addition to the engine 10, a lubricating liquid pump (pump) 11 adapted to draw lubricating liquid from a lubricating liquid tank 12 and send it to the engine 10. The engine 10 is in turn connected to the lubricating liquid tank 12 in order to allow recovery of the lubricating liquid. A filter 12 adapted to retain, in a conventional manner, impurities present in the lubricating liquid before it enters the engine for lubricating the same, is arranged between the pump 11 and the engine 10.

The example diagnostic system applied to the lubrication circuit is a diagnostic system based on the detection of the viscosity of the lubricating liquid.

According to a preferred embodiment, the diagnostic system comprises a viscometer 20, of conventional type, having an inlet 21 which is preferably arranged downstream of the filter 13 and at which, in use, the lubricating liquid has a pressure $P_m$, and an outlet 22 which is preferably in communication with the lubricating liquid tank 12 and at which the lubricating liquid has a pressure $P_t$ lower than the pressure $P_m$.

Figure 2:
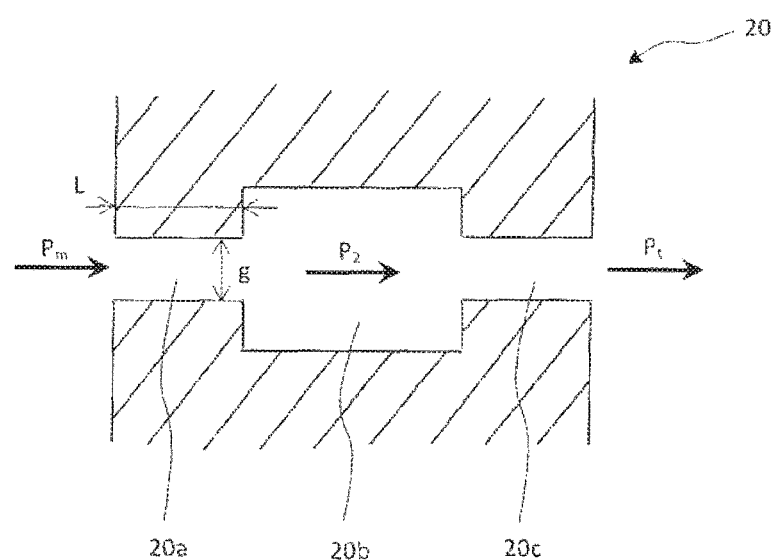
FIG. 2 is a schematic view of a viscometer used in a diagnostic system according to the present invention.

Referring to FIG. 2, the viscometer 20 has an inlet section 20a and an outlet section 20c between which a viscometer chamber 20b is arranged. The inlet section 20a has a geometry such that the lubricating liquid flow in this section is preferably of the laminar, or substantially laminar, type, whereas the outlet section 20c has a geometry such that the lubricating liquid flow in this section is preferably of the turbulent, or substantially turbulent, type.

The inlet section 20a has, for example, the shape of a tube having a length L and a rectangular cross-section with sides band g, wherein the side b has a length much greater than that of the side g. The flow rate of the liquid having with laminar flow through said section is given, in a conventional manner, by the following relation:

$$Q_{laminar} = \frac{P_i - P_c}{\mu} \frac{bg^3}{12L}$$

where $P_i$ is the pressure of the lubricant liquid at the inlet 21 of the viscometer 20 (equal to $P_m$ in the preferred embodiment described above), $P_c$ is the pressure of the lubricating liquid within the viscometer chamber 20b and μ is the viscosity of the lubricating liquid.

The outlet section 20c has, for example, the shape of an orifice having a cross-section A. The flow rate of the liquid having with turbulent flow trough said section is given, in a conventional manner, by the following relation:

$$Q_{turbulent} = AC_{ef}\sqrt{\frac{2P_c}{\rho}}$$

where $C_{ef}$ is a discharge coefficient and ρ is the density of the lubricating liquid.

As the flow rate of the lubricating liquid does not vary along its path (there are neither accumulations nor leakages of lubricating liquid), it is possible to equal the two flow rates $Q_{laminar}$ e $Q_{turbulent}$ thereby obtaining that the viscosity μ is given by the following relation:

$$\mu = \frac{P_i = P_c}{\sqrt{P_c}} \frac{bg^3}{12LAC_{ef}} \sqrt{\frac{\rho}{2}}$$

Considering $C_{ef}$ and ρ as being substantially constant, the only variable quantities on which viscosity is dependent are therefore the pressure $P_i$, at the inlet 21 of the viscometer 20 and the pressure $P_c$ within the viscometer chamber 20c.

According to another embodiment, the inlet 21 of the viscometer is provided in a portion of the lubrication circuit located downstream of the lubricating liquid pump 11 and upstream of the filter 13, where, in use, the lubricating liquid has a pressure $P_l$, whereas the outlet 22 is in communication with the lubricating liquid tank 13.

According to still another embodiment, the inlet 21 of the viscometer 20 is provided downstream of the filter 13, whereas the outlet 22 is provided in the portion downstream of the pump 11 and upstream of the filter 13.

The example diagnostic system comprises a temperature sensor 25, suitable for detecting the temperature of the lubricating liquid, an arrangement 26 for acquiring the date of last replacement of the lubricating liquid, and an arrangement 27 for determining an instantaneous condition of use of the engine 10.

A non-exhaustive and non-exclusive set of possible arrangements for determining the condition of use of the engine consists, for example, of sensors adapted to detect the rotation speed of the motor shaft, the torque and/or the power of the engine, the speed of the vehicle, the distance traveled by the vehicle and the temperature outside the engine. Such sensors are usually already present on the vehicle engine.

The diagnostic system further comprises a control unit 28 connected to the viscometer 20, to the temperature sensor 25, to the arrangement 26 for acquiring the date of last replacement of the lubricating liquid, and to the arrangement 27 for determining an instantaneous condition of use of the engine 10. The control unit 28 is adapted to acquire, by means of the sensors, the state of the lubricating liquid, said state being preferably defined by the viscosity of the lubricating liquid for a given temperature of the lubricating liquid, a given date of last replacement of the lubricating liquid and a given condition of use of the engine.

The diagnostic system further comprises a database 29, preferably arranged aboard the vehicle, in which the control unit 28 stores the detected states of the lubricating liquid and which is further adapted to contain reference viscosity values for at least a given temperature of the lubricating liquid, a given date of last replacement of the lubricating liquid and a given condition of use of the engine.

According to an example embodiment, the viscosity reference values of are viscosity values that are considered optimal in a certain condition of lubricating liquid and use of the engine 10. The database therefore contains a map of the optimal viscosity values associated with certain values of parameters describing the condition of the lubricating liquid and of use of the engine, such as, for instance, the temperature of the lubricating liquid, the date of last replacement of the lubricating liquid, in a certain condition of use of the engine, to be compared with the instantaneous values detected by the aforesaid sensors.

According to another embodiment, the viscosity reference values are viscosity mean values of a fleet of same or similar vehicles in the same or similar condition of the lubricating liquid and of us of the engine, given, for example by the temperature of the lubricating liquid, by the date of last replacement of the lubricating liquid, in a certain condition of use of the engine, to be compared with the instantaneous values detected by the aforesaid sensors.

The control unit 28 is further configured to evaluate the state of the lubricating liquid, as defined above, by comparing the viscosity of the lubricating fluid with the viscosity values stored in the database in the same or similar condition of the lubricating liquid and of use of the engine.

Depending on the evaluation of the state of the lubricating liquid in a certain condition of use of the engine 10, the control unit 28 is configured to generate alert signals or to activate specific functions to intervene on the state of the lubricating liquid. In general, these signals and functions are activated when a viscosity is detected lower than certain suitably selected threshold values, in a given condition of the lubricating liquid (temperature and date of last replacement) and of use of the engine.

The signals and functions provided for by the present invention include:
  signal indicating that replacement of the lubricating liquid is required;
  carrying out cycles of regeneration of the filter 13;
  signal indicating that speed reduction is required;
  carrying out the "recovery" mode of the engine 10;
  varying the flow rate of lubricating liquid directed to the engine 10;
  signal indicating that addition of additives to the lubricating liquid is required;
  adding additives to the lubricating liquid.

The activation of the signals and functions listed above is illustrated in greater detail here below.

The control unit 28 is configured to generate a signal indicating that replacement of the lubricating liquid is required when a viscosity of the lubricating liquid, in a certain condition of temperature of the lubricating liquid and date of last replacement of the lubricating liquid, lower than a certain, suitably chosen critical value is detected. This liquid replacement signal can be activated aboard the vehicle (by means, for example, of indicator lights and acoustic signals) and/or remotely transmitted by means of a suitable transmitting unit 30 connected to the control unit 28. For example, the liquid replacement signal can be transmitted to a support center, to the vehicle manufacturing company, to the manager of a vehicle feet to which the concerned vehicle belongs, and so on.

The control unit 28 is further configured to control the carrying out of cycles of regeneration of the filter 13 of the lubrication circuit, depending on the detected state of the lubricating liquid and the future use of the inner combustion engine 10.

The regeneration of the filter 13 of the lubrication circuit is the conventional process which allows combustion of particulate deposited within the filter 13, for example a DPF filter (diesel particulate filter) or a APF filter (anti-particulate filter), which are conventional. The combustion of such particulate takes place at temperatures of about 600-650° C., post-injections of fuel being effected in order to reach such temperatures. Such post-injections, however, have the drawback that they contaminate and dilute the lubricating liquid, thus causing deterioration thereof.

According to the present invention, the control unit is configured to receive, for example from a GPS 40 navigation device located aboard the vehicle, information concerning the path to be traveled by the vehicle and, on the basis of such path information, identify sections of the path in which it is preferable to carry out a regeneration cycle. Advantageously, such preferable sections of the path are those in which the engine is expected to be hotter, for example on the motorway or along uphill road sections, so as to make regeneration more efficient and consequently extend the life of the lubricating liquid.

The control unit 28 is further configured to activate, depending on the state of the lubricating liquid, a signal requiring speed reduction aboard the vehicle and/or activate a conventional "recovery" mode of the internal combustion engine 10. The "recovery" mode is a mode in which the engine runs at low speeds and is usually activated when anomalies are detected which might damage the engine, in order to preserve the engine. In the present invention, such mode is activated in order to prevent damages to the motor caused by a non-optimal lubrication.

The control unit 28 is further configured to vary, depending on the state of the lubricating liquid, the flow rate of the lubricating liquid supplied to the engine 10. This function is used for supplying the engine 10 with an appropriate amount of lubricating liquid. For example, if the engine has a particularly high temperature, the flow rate is advantageously increase in order to compensate for the decrease in viscosity of the lubricating liquid caused by the high temperature.

According to an example embodiment, the control unit 28 is capable of varying the flow rate of lubricating liquid by controlling variation of the displacement of a variable displacement pump for the lubricating liquid.

According to another example embodiment, the control unit 28 is capable of varying the flow rate of the lubricating liquid by actuating an electronic system of flow rate adjustment provided downstream of the lubricating liquid pump.

The control unit 28 is further configured to generate, depending on the state of the lubricating liquid, a signal requiring addition of additives to the lubricating liquid. The addition of additives to the lubricating liquid allows, in a conventional manner, to restore characteristics of said liquid which makes it again suitable for effectively carrying out the action of lubricating the engine. More particularly, the signal requiring addition of additives is generated when a viscosity of the lubricating liquid, in a certain condition of temperature of the lubricating liquid and date of last replacement of the lubricating liquid, lower than a certain critical value (said critical value is preferably higher than the viscosity critical value which triggers generation of the signal requiring replacement of the lubricating liquid, as described above) is detected. The signal requiring addition of additives can be activated aboard the vehicle and/or remotely transmitted by means of the transmitting unit 30 connected to the control unit 28. For example, the signal requiring addition of additives to the lubricating liquid can be transmitted to a support center, to the vehicle manufacturing company, to the manager of a vehicle fleet to which the concerned vehicle belongs, and so on.

The control unit 28, in alternative or in addition to generating the signal requiring addition of additives to the lubricating liquid, is further configured to activate said addition of such additives, which are dispensable by a suitable additive tank (not shown). Such addition of additives is activated by the control unit 28 either autonomously or upon a user's request.

According to a further aspect of the present invention, it is further possible to provide that the data concerning the state of the lubricating liquid and detected by the diagnostic system are used in suitable diagnostic models adapted to assess whether there are any problems in the lubrication circuit of the engine.

According to another example embodiment of the present invention, the database in the diagnostic system can be a remote database, not provided aboard the vehicle. In this case, the control unit 28, through the receiving/transmitting unit 30 will transmit the detected states of the lubricating liquid and the corresponding condition of use of the engine to the remote database and will receive from said database the viscosity reference values.

The example diagnostic systems as described and illustrated can be subject to further variants and modifications falling within the scope of the present invention.

The invention claimed is:

1. A diagnostic system for a lubrication circuit of an internal combustion engine of a vehicle, the system comprising:
   a viscometer configured to detect a viscosity of a lubricating liquid of the lubrication circuit;
   a temperature sensor configured to detect a temperature of the lubricating liquid;
   an arrangement configured to determine a condition of use of the engine;
   a database which stores viscosity reference values for at least given temperatures of the lubricating liquid, given dates of last replacement of the lubricating liquid, and given conditions of use of the engine; and
   a control unit configured to acquire a state of the lubricating liquid based on the detected viscosity and a lubricating liquid condition of the lubricating liquid, the lubricating liquid condition including the temperature of the lubricating liquid, a date of last replacement of the lubricating liquid, and the condition of use of the engine, and configured to assess the state of the lubricating liquid by comparing the detected viscosity of the lubricating liquid with the viscosity reference values stored in the database as a function of lubricating liquid temperature, date of last replacement of the lubricating liquid, and use of the engine,
   wherein the control unit is configured to control, depending on the detected state of the lubricating liquid, actuation of a regeneration cycle of a filter of the lubrication circuit.

2. The diagnostic system according to claim 1, wherein the arrangement configured to determine the condition of use of the engine includes at least one of: a sensor configured to detect a rotational speed of a drive shaft, a sensor configured to detect torque of the engine, a sensor configured to detect power of the engine, a sensor configured to detect a speed of the vehicle, a sensor configured to detect a distance traveled by the vehicle, or a sensor configured to detect a temperature outside the engine.

3. The diagnostic system according to claim 1, wherein the control unit is configured to activate, depending on the detected state of the lubricating liquid, a signal indicating that replacement of the lubricating liquid is required.

4. The diagnostic system according to claim 1, wherein the control unit is configured to, based on information about a path that the vehicle will have to travel, determine a section of the path in which to actuate the regeneration cycle of the filter.

5. The diagnostic system according to claim 1, wherein the control unit is configured to activate, depending on the state of the lubricating liquid, a signal aboard the vehicle indicating that reduction of a speed of the vehicle is required.

6. The diagnostic system according to claim 1, wherein the control unit is configured to activate, depending on the state of the lubricating liquid, a recovery mode of the internal combustion engine in which the engine operates at reduced speeds.

7. The diagnostic system according to claim 1, wherein the control unit is configured to vary, depending on the state of lubricant liquid and on use of the vehicle, a flow rate of the lubricating liquid supplied to the engine.

8. The diagnostic system according to claim 1, wherein the control unit is configured to generate, depending on the state of the lubricating liquid, a signal indicating that addition of additives to the lubricating liquid is required.

9. The diagnostic system according to claim 1, wherein the control unit is configured to activate an addition of additives to the lubricating liquid, said additives being dispensed by an additive tank connected to the lubrication circuit.

* * * * *